United States Patent [19]
Zabara

[11] Patent Number: 5,700,282
[45] Date of Patent: Dec. 23, 1997

[54] HEART RHYTHM STABILIZATION USING A NEUROCYBERNETIC PROSTHESIS

[76] Inventor: Jacob Zabara, 200 Locust, Apt. 22D, Philadelphia, Pa. 19106

[21] Appl. No.: 542,759

[22] Filed: Oct. 13, 1995

[51] Int. Cl.$^6$ .................................................. A61N 1/36
[52] U.S. Cl. .......................... 607/9; 607/118; 607/148
[58] Field of Search ............................. 607/44, 9, 14, 607/45, 42, 118, 148

[56] References Cited

U.S. PATENT DOCUMENTS

| | | |
|---|---|---|
| 3,421,511 | 1/1969 | Schwartz et al. . |
| 3,522,811 | 8/1970 | Schwartz . |
| 3,650,277 | 3/1972 | Sjostrand et al. . |
| 3,796,221 | 3/1974 | Hagfors . |
| 3,850,161 | 11/1974 | Liss . |
| 3,918,461 | 11/1975 | Cooper . |
| 4,702,254 | 10/1987 | Zabara . |
| 4,867,164 | 9/1989 | Zabara . |
| 4,890,617 | 1/1990 | Markowitz et al. . |
| 4,951,667 | 8/1990 | Markowitz et al. . |
| 4,998,974 | 3/1991 | Aker . |
| 5,025,807 | 6/1991 | Zabara . |
| 5,086,772 | 2/1992 | Larnard et al. . |
| 5,144,947 | 9/1992 | Wilson . |
| 5,154,172 | 10/1992 | Terry, Jr. et al. . |
| 5,179,950 | 1/1993 | Stanislaw . |
| 5,186,170 | 2/1993 | Varrichio et al. . |
| 5,199,428 | 4/1993 | Obel et al. ............................ 607/44 |
| 5,203,326 | 4/1993 | Collins ................................ 607/4 |
| 5,222,494 | 6/1993 | Baker, Jr. . |
| 5,522,854 | 6/1996 | Ideker et al. ....................... 607/14 |

FOREIGN PATENT DOCUMENTS 0 688 577 A1 12/1995 European Pat. Off. .
WO 93/21824 11/1993 WIPO .

OTHER PUBLICATIONS

Bilgutay et al., "Vagal Tuning: A New Concept in the Treatment of Supraventricular Arrhythmias, Angina Pectoris, and Heart Failure", *J. Thor. Cardiovas. Surg.* (Jul., 1968).

Potter et al., "Neuropeptides in Sympathetic Nerves Affect Vagal Regulation of the Heart", *News in Physiol. Sci.*, (Aug., 1994) 9:174–177.

Parsonnet et al., "Radio Frequency Stimulation of the Carotid Baroreceptors in the Treatment of Hypertension," Surgical Forum, pp. 125–127, Dec. 1966.

*Primary Examiner*—William E. Kamm
*Assistant Examiner*—Kennedy J. Schaetzle
*Attorney, Agent, or Firm*—Panitch Schwarze Jacobs & Nadel, P.C.

[57] ABSTRACT

Heart rhythm is stabilized within the heart's free running cycle by detecting arrhythmias in a mammalian subject, and then electronically stimulating the subject's vagus and cardiac sympathetic nerves. More specifically, vagus efferents are stimulated to directly cause heart rate to slow down, while cardiac sympathetic nerve efferents are stimulated to cause the heart rate to quicken. Simultaneously, afferents from vagus and/or cardiac sympathetic nerves induce the brain to employ the brain's natural mechanisms of heart rhythm control. Such nerve stimulation works in harmony with the body's natural mechanisms of heart rhythm control.

20 Claims, 1 Drawing Sheet

HEART RHYTHM STABILIZATION USING A NEUROCYBERNETIC PROSTHESIS

FIELD OF THE INVENTION

The invention is related to stabilizing heart rhythm using a neurocybernetic prosthesis, and more particularly to using a nerve stimulation technique to maintain heart rhythm within a heart's free running cycle.

BACKGROUND OF THE INVENTION

There are many instances in which a person's heart rhythm is not optimal for his or her well-being, and may even be life-threatening. Arrhythmias in which the heart rhythm is too fast include fibrillation, flutter and tachycardia. Arrhythmia in which the heart rhythm is too slow is known as bradyarrhythmia. In each of these instances, the body's mechanisms for maintaining the heart rate in the normal resting range, also known as the free running cycle, are somehow defective.

Various means have been disclosed and are in use to influence the heart to beat with a desired rhythm. Drugs are commonly used to influence heart rhythm. Thus, if a person has a chronic arrhythmic condition, drugs may be administered on a regular basis in an effort to control this problem. Alternatively, persons with one of these conditions may keep a drug, e.g., nitroglycerin, with them at all times to be taken whenever they sense that their heart rhythm is erratic. Although drug therapy is quite common, it has a significant number of shortfalls, including being somewhat nonspecific in that side effects may occur, and lacking a good correlation between the dosage needed and the dosage administered, among many other problems.

Another approach to heart rhythm regulation is to place electrodes directly onto heart tissue, to thereby send electronic signals to the heart. For example, a pacemaker is commonly used in instances when the heart rhythm is chronically arrhythmic. For treating bradycardia (slow heart rates), this approach is safe and highly successful, and is known as bradycardia pacing. On the other hand, tachycardia pacing is not as effective and is very risky, because the pacing may accelerate the heart rate into lethal fibrillation.

An Active Implantable Cardiac Defibrillator (AICD) is commercially available and is the treatment of choice in some cases. This unit combines tachycardia pacing with a backup defibrillation to be used in the event of fibrillation. However, these units are very complex and expensive, and thus not widely used.

There have been some reports of using electrodes to stimulate the vagus nerve, where such stimulation has an effect on heart rhythm. See, e.g., Bilgutay et al., *J. Thoracic Cardiovas. Surg.* 56 (1):71–82 (July 1968). Electrical stimulation of the vagus nerve causes nerve impulses to be sent to the heart, where the nerve impulses cause the heart rate to decrease. However, this approach to heart rhythm control suffers from the potential to overstimulate the vagus nerve and thus cause the person to experience possibly life-threatening bradyarrhythmia. Certainly, vagus nerve stimulation alone would not be a suitable treatment for bradycardia.

Drugs may be used to counteract bradyarrhythmia, as disclosed in Bilgutay, above, however drug therapy in this instance is usually not sufficiently timed or dosed to be effective. Alternatively, electrodes may be placed directly on both the heart and vagus nerve, where vagal stimulation serves to slow heart rate and electrodes on the heart provide pacing stimuli to increase heart rate as necessary. This latter approach to heart rate control, which entails a bradyarrhythmia pacemaker, is described in PCT publication number WO 93/21824 ("Medtronic"), which also describes prior art approaches to heart rate control, and discusses the Bilgutay paper. The Medtronic approach suffers from complex and invasive surgery to locate pacemaker electrodes inside the heart.

There is a need in the art for a process to counteract episodic and chronic heart arrhythmias, where the process would promptly respond to acute cases of arrhythmia.

SUMMARY OF THE INVENTION

The invention provides a process for stabilization of a heart rhythm in a human. The process comprises the steps of (a) monitoring the human's heart rhythm to detect arrhythmia; and in response to arrhythmia (b) sending at least one electronic signal simultaneously to the human's vagus and cardiac sympathetic nerves to stabilize the heart rhythm.

Another aspect of the invention is a process for stabilization of a heart rhythm in a human. The process comprises the steps of (a) programming a neurocybernetic prosthesis to periodically send electronic signals to one or more electrodes; and (b) contacting both of the human's vagus and cardiac sympathetic nerves with said one or more electrodes.

Still another aspect of the invention is a process for electrode placement in a human. The process comprises the step of placing at least one electrode in contact with both a vagus nerve and a cardiac sympathetic nerve of the human.

A further aspect of the invention is an apparatus for restoring a human's heart rhythm to the heart's free running cycle. The apparatus comprises a means for detecting a human's arrhythmia, said means in electronic communication with a neurocybernetic prosthesis. The apparatus also comprises a means for sending at least one electronic signal simultaneously to the human's vagus nerves and cardiac sympathetic nerves from the neurocybernetic prosthesis.

BRIEF DESCRIPTION OF THE DRAWINGS

The foregoing summary, as well as the following detailed description of the preferred embodiment of the invention, will be better understood when read in conjunction with the appended drawing. For the purpose of illustrating the invention, there is shown in the drawing an embodiment which is presently preferred. It should be understood, however, that the invention is not limited to the precise arrangements and instrumentalities shown.

In the drawing.

DETAILED DESCRIPTION OF PREFERRED EMBODIMENTS

Figure 1:
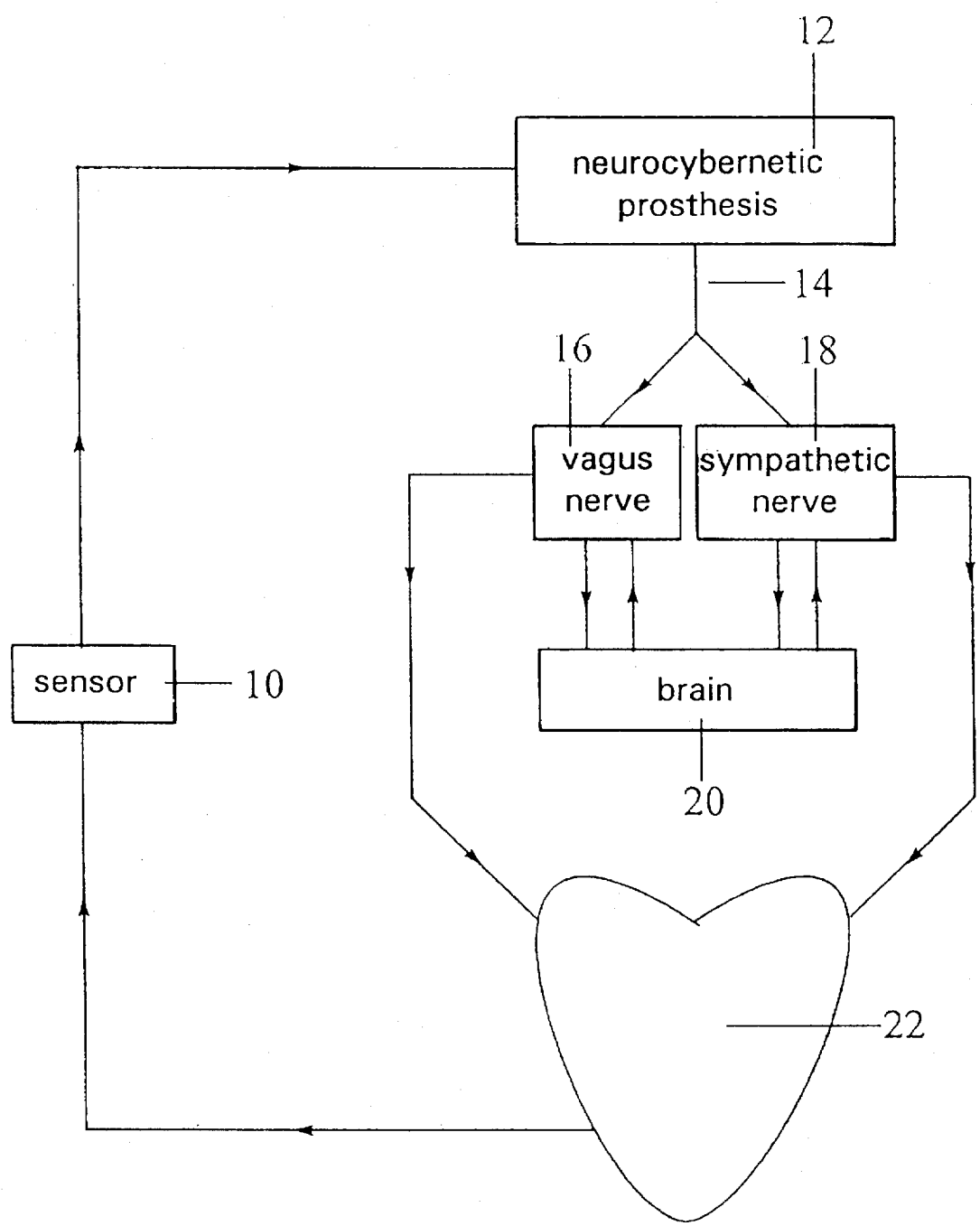
FIG. 1 is a highly schematic overview showing a feedback loop of the invention wherein heart rate data is received by a neurocybernetic prosthesis, which sends out an electronic stimulation to the vagus and cardiac sympathetic nerves to generate action potentials in those nerves leading to the heart and brain, to thereby affect heart rate.

The following discussion of the body's inherent mechanisms for heart regulation is provided as background to understanding the efficacy of the inventive method. In a healthy human subject, vagus and cardiac sympathetic nerves are intimately involved in automatically maintaining heart rate within a free running cycle. The vagal nerves as referred to herein include all nerves of the vagus efferent and afferent which are involved in regulation or stabilization of the heart, such as baroreceptor or chemoreceptor nerves, the direct efferent innervation of the SA or AV nodes, etc. For convenience, the cardiac sympathetic nerves as referred to herein will include the cervical sympathetic nerve trunk in the neck, and the stellate ganglia.

In general, stimulation of the heart by the vagus nerve leads to a decrease in heart rate, while stimulation of the heart by the cardiac sympathetic nerve leads to an increase in heart rate. The body uses the combined actions of the vagus and cardiac sympathetic nerves to assist in keeping the heart rhythm within the heart's free running cycle.

More specifically, the vagus and cardiac sympathetic nerves act on the heart's SA node, AV node, coronary flow and/or muscle contractility to thereby regulate heart rhythm. The vagal efferents produce a hyperpolarization of the SA Node and AV node, and an increase in coronary flow. The sympathetic efferents produce a depolarization of the SA node and AV node, and an increased muscle contractility. The cardiac sympathetic nerves can also increase the contractile force of the heart, which causes an increased benefit of a lower heart rate. The net effect of action potentials from the vagus and cardiac sympathetic nerves is to produce a summation of hyperpolarizations and depolarizations in the SA node and AV node, and an increase in coronary flow or muscle contractility, which maintains a steady heart rhythm.

Vagal regulation is coordinated with sympathetic nerve regulation of the heart. For instance, vagus stimulation can decrease the heart rate, depending upon the free-running cardiac cycle, and sympathetic stimulation can increase the heart rate. An optimum, or stabilized heart rate is realized by coordination of vagal and sympathetic stimulation. Each set of nerves acting independently might "overshoot" the set point for heart rate, as determined by specific demands, such as exercise. Thus, the human body naturally employs sympathetic stimulation, to act as a "buffer" to safeguard against possible bradycardia, or even bradyarrhythmias, which might be a consequence of inadvertent excessive vagal stimulation.

In broad overview, the present invention preferably provides for monitoring a subject's heart rhythm to detect episodes of arrhythmia, i.e., episodes of unstable or malignant rhythms where the heart deviates from its free running cycle. When arrhythmia is detected, the invention provides for a neurocybernetic prosthesis to simultaneously stimulate vagal and cardiac sympathetic nerves. As used herein, the term cardiac nerves refers collectively to the vagal and cardiac sympathetic nerves. This stimulation prompts the heart to return to its free running cycle. The preferred subject is a human.

FIG. 1 provides a highly schematic overview of a preferred embodiment of the invention. As shown in FIG. 1, a sensor 10 detects a subject's heart rhythm, and feeds that information into a neurocybernetic prosthesis 12. When the heart's rhythm is not within an acceptable range, the neurocybernetic prosthesis 12 is preprogrammed to respond by sending electronic stimulation through one or more wires and ultimately one or more electrodes (collectively 14) impinging on at least one vagus nerve 16 (a parasympathetic nerve) and at least one cardiac sympathetic nerve 18. The electronic stimulation induces vagus and cardiac sympathetic nerves to send action potentials to both the brain 20 and the heart 22.

Action potentials sent to the heart 22 will directly affect heart rate. Action potentials sent to the brain 20 will prompt the cardiovascular centers of the brain (not shown), including the nucleus of tractus solitarius, through the so-called recruitment effect or recruitment response, to send action potentials back through vagus and cardiac sympathetic nerves, to impinge on the heart and thereby encourage the heart to return to its free running cycle. This restabilization of heart rhythm is detected by the sensor 10, which completes the loop. In FIG. 1, the arrows show the direction of information flow.

Various components of an apparatus useful in the inventive method, and where these components may be located, will now be described. The invention employs a neurocybernetic prosthesis that, in response to certain stimuli, will send electronic signals to the cardiac nerves.

The prosthesis is preferably capable of distinguishing between various different stimuli, as discussed below, and will initiate electronic signals in response to the specific stimulus received according to preprogrammed parameters. Thus, the neurocybernetic prosthesis can be controlled by its programming functions to adjust for the individual requirements of the subject and type of arrhythmia.

Neurocybernetic prostheses suited for the inventive method are well-known in the art and commercially available. A preferred neurocybernetic prosthesis was originally disclosed in U.S. Pat. Nos. 5,025,807; 4,867,164 and 4,702,254. The prosthesis may be located external to the body of the subject, or implanted in the subject's body.

In instances where a physician determines that the subject has serious, possibly life-threatening arrhythmias, it may be preferred to implant the prosthesis within the subject's body, in order to provide permanent alleviation of the subject's chronic condition. A preferred implantable prosthesis is described in detail in U.S. Pat. No. 5,154,172, the entire disclosure of which is incorporated herein by reference. A suitable implantable prosthesis may be obtained from Cyberonics, Inc. of Webster, Tex., as Model 100 NCP Pulse Generator.

Connected to the prosthesis are one or more wires that terminate with one or more electrodes. The inventive method entails the simultaneous electronic stimulation of both vagus and cardiac sympathetic nerves, including both afferents (nerves that send action potentials to the brain) and efferents (nerves that send action potentials to the heart) of at least one of these nerve types, and preferably both types of nerves. The inventive method thus encompasses the use of at least one electrode, preferably one or two electrodes, to contact the vagus and cardiac sympathetic nerves.

According to the method, an electrode is contacted with one or more nerves, where any electrode that will cause little or no physical damage to the nerve is suitable according to the invention. Exemplary electrodes include helical and patch electrodes, where both of these electrode types are well known in the art and commercially available. A helical electrode is presently preferred for the inventive method, and is disclosed in, e.g., U.S. Pat. Nos. 4,573,481 and 5,154,172. Preferably, the diameter of the helical electrode should be about equal to or somewhat larger than the diameter of the nerve or nerve bundle being stimulated by the electrode.

The exact site of electrode placement on the vagus and cardiac sympathetic nerve is not critical. As electrode placement entails a surgical procedure, sites for electrode placement are preferably selected so as to minimize the invasiveness, and hence the risk to the subject, of the surgical operation. As surgeons are well aware, cardiac sympathetic nerves come out of the cervical-thoracic portion of the spinal cord. A cardiac sympathetic nerve is contained within, or adjacent to, the cervical sympathetic trunk, with which it travels before branching off to the heart. The superior and inferior cardiac nerves of the vagus are contained within the cervical vagus, before branching off to the heart. It is thus possible to capture all of these nerves within the same limited operative procedure in the neck, since both vagal and sympathetic trunks lie along the carotid artery, they can easily be dissected free of surrounding tissue and placed within electrodes, for stimulation. Such surgery is familiar to surgeons who preform typical neurosurgical procedures such as in cervical carotid obstruction.

Thus, in a preferred embodiment of the invention, a single electrode, or a pair of electrodes, may be utilized to include both the sympathetic nerve trunk and cervical vagus nerves according to the invention. A single electrode is the simplest, or most benign configuration; however, it may not be as effective as separate electrode placements. A single electrode provides for unipolar stimulation, where the electrode acts as the cathode and the prosthesis itself acts as the anode.

According to another preferred embodiment of the invention, two electrodes may be contacted with vagus and cardiac sympathetic nerves. The first electrode may be located as described above, on the cervical vagus above the branching of the superior cardiac nerve. The second electrode may be placed above or below the branching of the superior cardiac nerve, to achieve bipolar stimulation. Bipolar stimulation is the placement of two electrodes, where one is cathodal and the other is anodal. Preferably, cathodal and anodal spiral electrodes are placed in adjacent positions around the combined vagus and cervical sympathetic nerves. The separate electrode placement may utilize conduction optimization, as discussed later, to individually activate vagal or cardiac sympathetic nerve afferents to achieve the recruitment responses.

The diagnosis of the type of arrhythmia will determine whether A-V or S-A node is primarily involved, and whether the right or left vagus is appropriate for stimulation. The electrode proximal to the heart will be the cathode if it is necessary to optimize efferent cardiac nerve activation. However, the electrode distal from the heart will be cathodal if it is necessary to optimize activation of afferent cardiac nerves for the recruitment response the heart. Thus, to maximize efferent nerve stimulation, the cathodal electrode may be placed proximal to the heart, while to maximize afferent nerve stimulation, the cathodal electrode may be placed proximal to the brain.

Although there is extensive overlap in the innervation areas of the heart by the right and left vagus, the right vagus innervates the A-V node more extensively, and the left vagus innervates the S-A node more prominently. Therefore, the right or left vagus can be selectively stimulated, depending on the origin and nature of the arrhythmia or fibrillation, by placing the electrodes on either the right or left branch. If necessary, electrodes could be placed on both the right and left branches, and the device could be programmed to respond appropriately.

The superior and inferior cardiac nerves of the vagus can be stimulated individually or together, for an optimum result, dependent upon the type of arrhythmia and conditions necessary for re-stabilization. For instance, if the arrhythmia is a premature ventricular contraction (PVC), the electrodes would be connected to the right cervical vagus and to the cervical sympathetic trunk in order to stabilize the rhythm.

An optional but preferred method of the invention, denoted the preventive mode, employs an electrode as a sensor to detect electrical signals from the heart. The electrode sensor is placed on either the atrium or ventricle to monitor and detect heart rhythms, force of contraction, EKG, time delays between EKG events, amplitudes of EKG events and pulse rate, any or all of which may indicate the need for cardiac nerve stimulation. Thus, the electrode sensor may detect the subject's heart rhythm as measured, e.g., by the subject's electrocardiogram (EKG) or pulse. EKG detection is described extensively in patents and patent applications relating to pacemakers. See, e.g., WO 93/21824, the disclosure of which is fully incorporated herein by reference. Additionally, sensors could be useful to detect the pulse from blood flow. This may be required for some conditions, as an electrical signal (e.g., EKG) does not closely associate with heart contraction and blood flow. As another alternative, a sensor could be used that monitors the impedance of the subject's heart. Such sensors are well known in the art.

A sensor is not necessarily present according to the inventive method. Thus, in one embodiment, the neurocybernetic prosthesis may be activated only in response to external stimulus, where such external stimuli may be provided by, e.g., the subject or a treating physician, who may override the programmed circuitry of the prosthesis in appropriate instances as described below. Thus, in addition to the preventive mode of the device, it is possible to have an interruption mode. The interruption mode would be utilized during the occurrence of an on-going arrhythmia to re-stabilize the rhythm. When the subject becomes aware that an arrhythmia is occurring, the subject can apply a magnet over his chest, which would cause a reed switch in the device to initiate the device's output. The output would be based on a programmed set of parameters appropriate for that particular subject.

Alternatively, or in addition, the neurocybernetic prosthesis may emit electronic signals on a continuous but periodic basis. This is preferred in instances where the subject suffers from chronic heart arrhythmia. In this instance, a physician must determine the proper electronic stimulation protocol for the subject, and have the prosthesis programmed accordingly. Procedures for making these determinations are known to physicians.

The following section identifies and describes heart rhythm disorders that are amenable to treatment by the inventive method. The method of the invention is useful to counteract arrhythmias such as atrial fibrillation, ventricular fibrillation, atrial tachycardia and ventricular tachycardia. Vagal stimulation has been indicated in studies to increase coronary flow either indirectly, by changing the heart rate or force of contraction, or directly, by increasing the diameter of the coronary blood vessels. Thus, the method may also be used when arrhythmia is due to decreased coronary flow.

An important aspect of the inventive method employs stimulation of selected nerve efferents to influence heart rhythm. Specifically, these selected nerve efferents are the cardiac vagal and cardiac sympathetic efferents, which may be stimulated together, or sometimes individually. Thus, the invention provides for the stimulation of the efferents of the vagus and cardiac sympathetic nerves to prevent or interrupt atrial or ventricular arrhythmias, including tachycardia, fibrillation or flutter. Upon electronic stimulation of the vagal nerve efferents, nerve impulses are sent to the heart which cause the heart rate to slow down.

However, it may happen that the heart rate slows down too much in response to the vagal stimulation, and this effect can be as bad, if not worse, for the subject as having a heart that is beating too fast. Thus, the invention also provides for stimulation of the cardiac sympathetic nerves, which slows down the heart rate. The sympathetic stimulation can also increase contractile force of the heart, which indirectly causes an increased cardiac output with the benefit of a lower heart rate.

When the efferents of the vagus and cardiac sympathetic nerves are electronically stimulated, these efferents send action potentials directly to the heart, and particularly to the SA node of the heart. Vagal stimulation of the SA node will cause node polarization, and thus a slowing of the heart rate, while cardiac sympathetic nerve stimulation of the SA node will cause depolarization of the node, and thus encourage a quickening of the heart rate.

Stimulation of selected nerve afferents is a second important part of the inventive method. Stimulation of the vagal and cardiac sympathetic nerves according to the invention accomplishes more than merely the direction of impulses to the heart. Due to proper electrode placement according to the invention, nerve impulses are also sent to the brain whenever arrhythmia is detected by the neurocybernetic prosthesis. Brain stimulation prompts the brain to exert its own natural mechanisms of heart rhythm control, which the brain was otherwise unable to effectively accomplish. Upon stimulation, the brain will be prompted to respond to the arrhythmia in its usual manner, i.e., by sending action potentials through the vagal and cardiac sympathetic nerves, by releasing hormones, etc. Nerve stimulation according to the invention thus recruits the brain's natural heart rate control mechanisms in an effort to combat arrhythmia, where this effort will be referred to herein as the recruitment effect or response.

Since the influence of the recruitment effect on the heart will arrive with a delay (from the time of stimulation onset), the effect initiated by efferent cardiac nerve stimulation can be prolonged or intensified through the recruitment effect achieved through afferent stimulation. Also, the recruitment effects will be coordinated in the cardiovascular centers of the brain with sympathetic activation or deactivation to optimize the overall effect on the heart.

Thus, according to the invention, the neurocybernetic prosthesis can simultaneously affect the cardiac nerves directly (sympathetic and vagus efferents), and produce the recruitment response by affecting vagal or sympathetic afferents to the brain.

The recruitment effect in the brain produces a relatively long-lasting coordination of both vagal and cardiac sympathetic nerve activity on the heart. In addition, due to reciprocal pathways to the cortex, brain stimulation produces a conditioning response over repeated stimulations which becomes incorporated into the inherent cardiovascular auto operation.

By stimulating both of nerve afferents and efferents of vagus and cardiac sympathetic nerves, the full benefits of the inventive method are achieved. A synchronous effect on heart rate is produced by simultaneous stimulation of efferents of both vagal and sympathetic cardiac nerves. This effect reaches a peak almost immediately but is of relatively short duration. A recruitment effect on heart rate is produced by stimulation of vagal, and optionally cardiac sympathetic afferent fibers to the brain causing both vagus and cardiac sympathetic efferent nerve discharges. This effect reaches a peak slowly but is of relatively long duration. The occurrence of both effects together, synchronous and recruitment, causes the most effective control of heart rate. This combined stimulation may be called rate convergence because it causes convergence of the heart rate to a resting, stable rhythm based on free-running cycling of heart contractions.

The cardiac sympathetic nerves contain fewer afferents than are in the vagus nerves. Thus, stimulation of vagus nerves will likely provide more recruitment effect than will stimulation of cardiac sympathetic nerves. According to the invention, sufficient recruitment effect may be achieved merely by stimulating afferents of the vagus nerves, however stimulating afferents of the cardiac sympathetic nerves in addition to vagal afferents is preferred according to the invention.

The following protocol can be employed to stimulate the nerves and thus achieve the beneficial results of the inventive method. After electrodes have been placed around the selected nerves as described above, a stimulation regime must be developed. In general, the current, frequency, pulse width, period, duration and rate of the electric signals may be varied. As used herein, the current of the electric signal refers to how many milliamperes are being delivered, and is typically about 1.0 to 30 milliamperes, but can range from about 0.1 to about 5 milliamperes. As used herein, the frequency of the signal refers to how many cycles per second make up the current, and is typically about 10 to about 30 cycles per second, but can range from about 5 to about 300 cycles per second. As used herein, the pulse width refers to how long a single pulse will last, and can vary between about 0.05 and 1 millisecond. As used herein, the period of stimulation refers to how often a continuous signal is sent to the electrode. For example, a continuous stimulating signal might be sent once a minute, or twice an hour, etc. As used herein, the duration of stimulation refers to how long a single continuous stimulation will last. For example, a stimulating signal might be given for a duration of 10 seconds or 30 seconds. As used herein, the rate of stimulation refers to how many electric pulses are sent to the electrode, every second, to provide a single continuous stimulation. Thus a pulse regime might be for a duration of 30 seconds, provided to the subject with a period of once per hour, using a constant current at 2 milliamperes with a pulse width of 500 microseconds and frequency of 20 cycles per second.

A suitable set of initial settings include stimulation at 30 Hz and 2.0 milliamperes, with a 200 msec pulse width for 30 seconds every 5 minutes continuously. During the subject's periodic visit to a hospital, the neurocybernetic prosthesis may be interrogated with a wand according to standard procedures known in the art, and the subject's EKG and blood pressure may be measured. The subject's comfort level will be determined, and if the subject is not uncomfortable, the current may be increased by about 0.5 milliamperes. The subject may be given a magnet, allowing the subject to voluntarily turn on and off the neurocybernetic prosthesis.

When action potentials are conducted in both afferent and efferent nerves, then conduction optimization may be used to individually activate either the afferents or efferents of these nerves. Conduction optimization is dependent on settings of current, frequency and pulse width to determine which pathway, either afferents or efferents and afferents, is activated. For example, increasing the frequency can put slower conduction velocity nerves into refractoriness and a low voltage activates only low threshold nerves. Also, in the bipolar electrode placement, with the positive electrode proximal to the brain, the pulse width can be increased to prevent action potentials from reaching the brain to produce the recruitment response.

The direct effects on the heart can be further discriminated by action on the SA node, AV node (and bundle of His) or coronary arteries. This selective action is based on adjusting the distance between electrode activation points, intensity of current, frequency of pulses, or polarity of electrodes. The conduction velocity of nerves in the vagus is approximately 0.5–80 meters per second, where the highest conduction velocity nerves are activated with the least stimulating current, the refractory period of the lowest conduction velocity nerves are longest, so that frequency discrimination is possible. The distance between electrode activation points can determine which potentials are transmitted past the anodal electrode.

The therapeutic method of the invention is particularly suited to achieving the goal of preventing arrhythmias or fibrillation in a subject who has been diagnosed by his physician as encountering such arrhythmias on a periodic basis. In these instances, the subject may benefit from a treatment regime that includes a 24 hour stimulation cycle, with the parameters of stimulation adjusted to the specific type and nature of the arrhythmia.

The rationale for this type of stimulation is based on the following analysis. The problem is that the parasympathetic nerves or vagus, on their own, cannot stabilize the heart rate, either because of a problem in the heart, such as ischemia, or a problem in the central regulation of the autonomic nerves. It is possible by periodic stimulation to reestablish this central regulation, and overcome even inherent destabilization in the heart, such as that caused by ischemia.

That a 24-hour stimulation cycle can stabilize the heart in humans is supported by the work of Uthman et al. "Efficacy and Safety of Vagus Nerve Stimulation in Patients with Complex Partial Seizures" *Epilepsia* (1990) 31 Suppl 2:544–550; Kamath et al. "Effect of Vagal Nerve Electrostimulation on the Power Spectrum of Heart Rate Variability in Man" *PACE Pacing Clin. Electrophysiol.* (Feb. 1992) 15 (2):235–243; and Kamath et al. "Neurocardiac Responses to Vagalafferent Electrostimulation in Humans" *PACE Pacing Clin. Electrophysiol.* (Oct. 1992) 15 (10 Pt. 2):1581–1587, which was performed on epileptic patients with complex partial seizures. Cardiac effects of chronic intermittent vagal stimulation in the conscious human with complex partial seizures were investigated with an EKG and 24 hour Holter monitor, during baseline and after 8 weeks of stimulation. There were no notable changes in the minimum, maximum, or average heart rates. There were no notable changes in EKG morphology in any of the subjects. Subjects were also stimulated during EKG recording, using the following parameters: 1–5 mA, 10–50 Hz, 250 us pulse width, for 84 sec. periods. No changes were observed during or immediately after stimulation. Premature atrial contractions (PAC), premature ventricular contractions (PVC) and atrioventricular conduction times (PR) were compared with baseline, and demonstrated interesting results. There appeared to be a decrease in both PAC and PVC in certain subjects after stimulation. In one subject, PVC decreased from 6/h to 3/h; in another, PAC decreased from 14/h to 5/h; in another, PAC, decreased from 6/h to 3/h. Kamath et. al conclude that an elevated vagal tone brought about by vagal stimulation in high risk coronary subjects may afford protection from life-threatening arrhythmias.

The inventive method does not interfere with the body's natural mechanisms at heart rhythm control. It is not always undesirable for heart rhythm to deviate from its free running cycle. For example, exercise desirably causes the heart rate to increase. Also, many emotional states, such as fear or anger, cause a desirable increase in heart rate. In each of these instances, an increase in heart rate is desirable as the corresponding increased blood flow helps the body respond to the demands being placed upon it. When the demands have subsided, the heart rate returns to the free running cycle.

It appears that the inventive method does not change the heart rate when the body's natural regulatory mechanisms are in balance. For instance, epileptic patients fitted with a vagal stimulator as described in U.S. Pat. Nos. 5,025,807; 4,867,164; and 4,702,254 appeared to display virtually no change in heart rate. Thus, during normal regulation, neurostimulation does not disturb this essential balance, but during abnormal rhythm, nerve stimulation provides the missing regulation to restore heart rhythm balance. The heart is particularly responsive to vagal stimulation if the heart is beating very quickly.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A process for stabilization of a heart rhythm in a human comprising the steps of
   (a) monitoring the human's heart rhythm to detect arrhythmia; and in response to arrhythmia
   (b) sending at least one electronic signal simultaneously to the human's vagus and cardiac sympathetic nerves to stabilize the heart rhythm.

2. The process of claim 1 further comprising the step of controlling the sending of the at least one electronic signal to induce the human's heart to have a rhythm within the heart's free running cycle.

3. The process of claim 1 wherein the sending of the at least one electronic signal comprises sending the signal to both the afferents and efferents of the vagus and cardiac sympathetic nerves to induce action potentials.

4. The process of claim 1 wherein the at least one electronic signal is delivered to the human's vagus and cardiac sympathetic nerves by way of a single electrode in contact with the vagus and cardiac sympathetic nerves.

5. The process of claim 1 wherein the at least one electronic signal is delivered to the human by a first electrode contacting the vagus nerve and a second electrode contacting the cardiac sympathetic nerves.

6. The process of claim 1 wherein a sensor monitors the human's heart rhythm to detect a heart rhythm outside of the heart's free running cycle, and upon detecting the heart rhythm the sensor sends an electronic signal to a neurocybernetic prosthesis, whereupon the prosthesis sends at least one electronic signal simultaneously to the vagus and cardiac sympathetic nerves to stabilize the heart rhythm.

7. The process of claim 6 wherein the sensor is programmed to send an electronic signal to the prosthesis upon detection of at least one occurrence of tachycardia, fibrillation, flutter or bradyarrhythmia.

8. A process for stabilization of a heart rhythm in a human comprising the steps of
   (a) programming a neurocybernetic prosthesis to periodically send electronic signals to one or more electrodes; and
   (b) contacting both of the human's vagus and cardiac sympathetic nerves with of said one or more electrodes.

9. The process of claim 8 wherein one electrode contacts both of the vagus and cardiac sympathetic nerves.

10. A process for electrode placement in a human comprising the step of placing at least one electrode in contact with both a vagus nerve and a cardiac sympathetic nerve of the human.

11. The process of claim 10 wherein the at least one electrode is contacted with the vagus and cardiac sympathetic nerves in the human's neck region.

12. The process of claim 10 wherein afferents and efferents of both the vagus and cardiac sympathetic nerves are contacted by the at least one electrode.

13. The process of claim 10 wherein the at least one electrode is a single electrode.

14. The process of claim 10 wherein the at least one electrode are bipolar electrodes.

15. An apparatus for restoring a human's heart rhythm to the heart's free running cycle comprising means for detecting a human's arrhythmia, said means in electronic communication with a neurocybernetic prosthesis, and means for sending at least one electronic signal simultaneously to the human's vagus nerves and cardiac sympathetic nerves from the neurocybernetic prosthesis.

16. The apparatus of claim 15 wherein the means for sending at least one electronic signal is an insulated wire terminating in a single electrode.

17. The apparatus of claim 15 wherein the means for sending at least one electronic signal is two wires, each wire terminating in a bipolar electrode.

18. The apparatus of claim 15 wherein the means for detecting a human's arrhythmia is a sensor that monitors the human's EKG.

19. The apparatus of claim 15 wherein the means for detecting a human's arrhythmia is a sensor that monitors the human's blood flow.

20. The apparatus of claim 15 wherein the means for detecting a human's arrhythmia is a sensor that monitors the impedance of the human's heart.

* * * * *